(12) United States Patent
Sherva et al.

(10) Patent No.: US 8,565,884 B2
(45) Date of Patent: Oct. 22, 2013

(54) IMPLANTABLE MEDICAL DEVICE AND METHOD OF MOLDING

(75) Inventors: Todd Garfield Sherva, Ham Lake, MN (US); Henri G. Asselin, Jr., Lowell, MA (US); Roger J. White, Lexington, MA (US); Brendan Arash Zarechian, Melrose, MA (US); Donald Eric Welling, Amesbury, MA (US); Todd R. Beaupre, Reading, MA (US); Christopher M. Haenisch, Fridley, MN (US)

(73) Assignee: Accellent Inc., Wilmington, MA (US)

( * ) Notice: Subject to any disclaimer, the term of this patent is extended or adjusted under 35 U.S.C. 154(b) by 51 days.

(21) Appl. No.: 13/296,131

(22) Filed: Nov. 14, 2011

(65) Prior Publication Data
US 2012/0123497 A1      May 17, 2012

Related U.S. Application Data

(60) Provisional application No. 61/413,933, filed on Nov. 15, 2010, provisional application No. 61/507,551, filed on Jul. 13, 2011.

(51) Int. Cl.
*A61N 1/02*      (2006.01)

(52) U.S. Cl.
USPC .............................................. 607/37; 607/36

(58) Field of Classification Search
USPC ............ 29/825, 841, 842; 439/736, 884, 885, 439/909; 607/36, 37
See application file for complete search history.

(56) References Cited

U.S. PATENT DOCUMENTS

| | | |
|---|---|---|
| 4,884,980 A | 12/1989 | Bensing |
| 4,983,344 A | 1/1991 | Brown |
| 5,453,029 A | 9/1995 | Moldenhauer |
| 5,679,026 A | 10/1997 | Fain |
| 5,926,952 A | 7/1999 | Ito |
| 6,219,913 B1 | 4/2001 | Uchiyama |
| 6,601,296 B1 | 8/2003 | Dailey et al. |
| 7,309,262 B2 | 12/2007 | Zart et al. |
| 7,489,968 B1 | 2/2009 | Alexander et al. |
| 7,654,843 B2 | 2/2010 | Olson et al. |
| 2007/0087637 A1* | 4/2007 | Zart et al. ...................... 439/736 |
| 2008/0303728 A1 | 12/2008 | Lee et al. |

FOREIGN PATENT DOCUMENTS

WO      0199239      12/2001

OTHER PUBLICATIONS

PCT Search Report dated Feb. 13, 2002, for International Patent Application No. PCT/US01/19606, filed Jun. 20, 2001 (WO2001099239A3); 4 pages.

* cited by examiner

*Primary Examiner* — Brian T Gedeon
(74) *Attorney, Agent, or Firm* — Ganz Law, PC

(57) ABSTRACT

An implantable medical device that includes a first molded portion and a second molded portion fusion bonded to the first molded portion at an interface. The molded portions each are based on a moldable plastic material. A component, e.g., an electrical component, for the implantable device has at least one section disposed at the fusion-bonded interface of the first molded portion and the second molded portion so that the electronic component is fusion bonded to one or both portions at the interface.

38 Claims, 11 Drawing Sheets

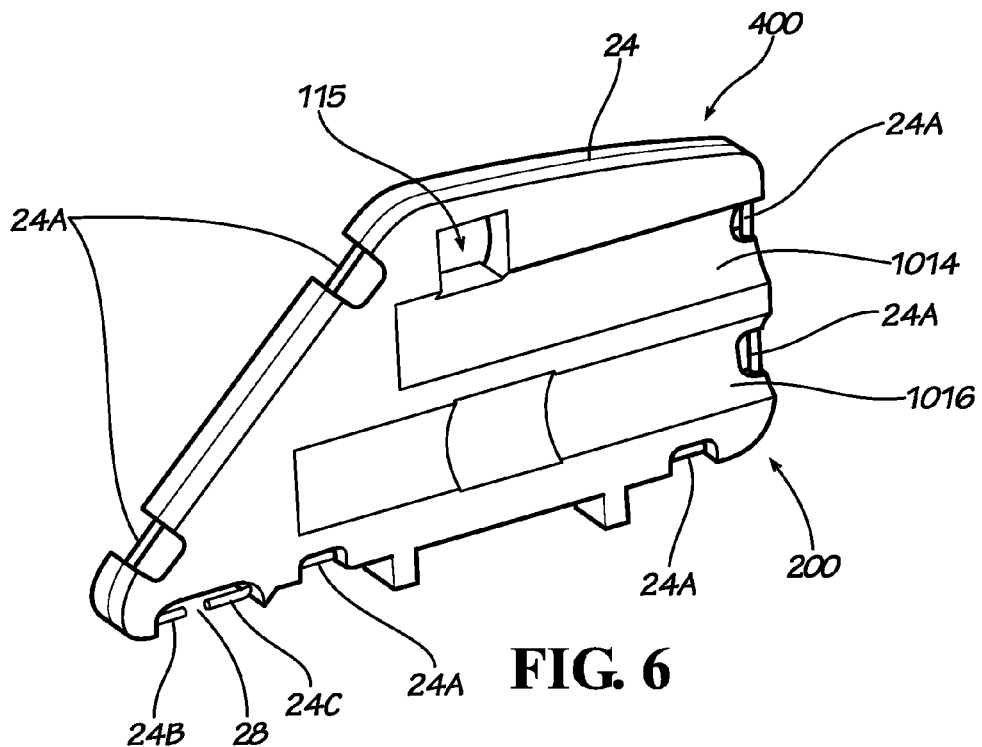
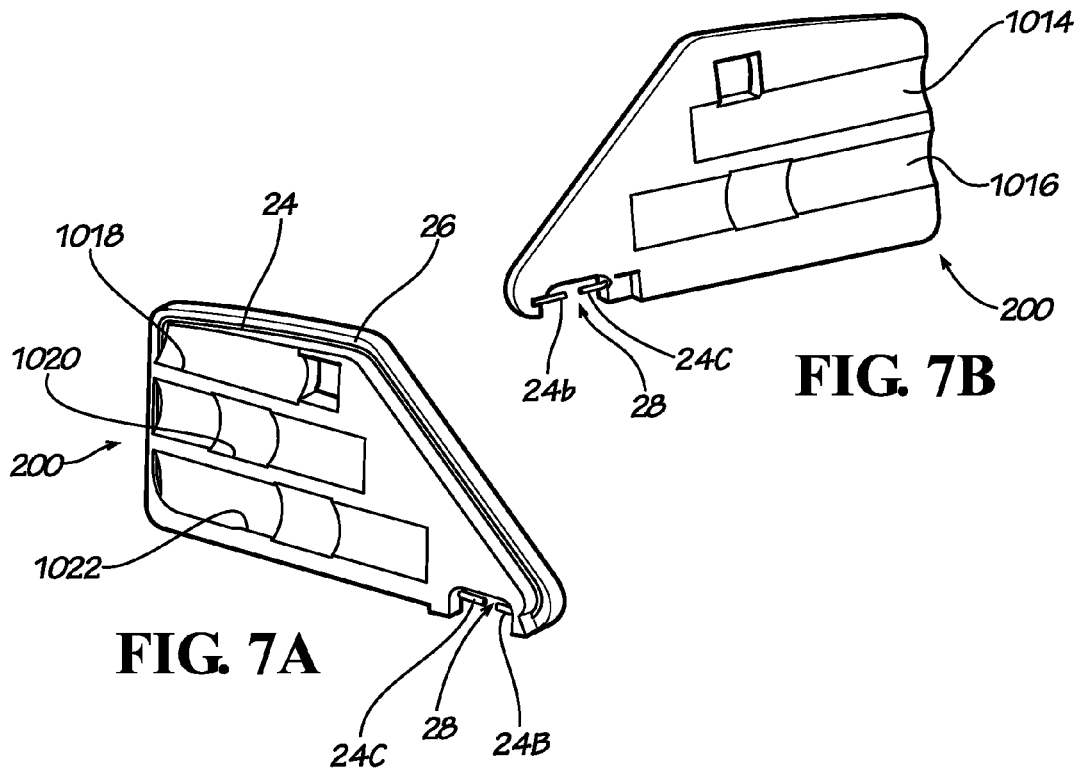
FIG. 6
FIG. 7A
FIG. 7B

IMPLANTABLE MEDICAL DEVICE AND METHOD OF MOLDING

CROSS-REFERENCE TO RELATED APPLICATIONS

This application claims the benefit of and priority to U.S. Provisional Patent Application Nos. 61/413,933, filed Nov. 15, 2010, and 61/507,551, filed Jul. 13, 2011, the contents of which applications are hereby incorporated by reference in their entirety, as if recited in full herein, for all purposes.

BACKGROUND

The inventive subject matter generally relates to implantable medical devices. It particularly relates to implantable devices made of molded plastics and having integrated electronics components, such as RF antennae, conductive elements, functional devices (e.g., resistors, semiconductor chips, RF devices, etc.), and optical guides (e.g., optical fiber).

The inventive subject matter is particularly suited for use with implantable devices for Cardiac Rhythm Management (CRM). Cardiac Rhythm Management Devices (CRMs) generally are small devices that are implanted into a patient's thoracic area. Modern CRM devices typically have a maximum length under 100 mm and a minimum volume of approximately 30 cc.

They send signals to cardiac tissue to stimulate it in response to sensed rhythms. Classes of CRM devices include, among other devices, implantable pacemakers and Implantable Cardiac Difibrillators (ICDs). A pacemaker monitors the electrical impulses in the heart. When needed, it delivers electrical pulses to make the heart beat in a more normal rhythm. A pacemaker may be helpful when the heart beats too slowly or has other abnormal rhythms. An ICD is a device that monitors heart rhythms. If it senses dangerous rhythms, it delivers shocks. Many ICDs record the heart's electrical patterns when there is an abnormal heartbeat. This can help a doctor plan future treatment.

A variety of implantable medical devices have emerged over the decades. Implantable devices are man-made, in contrast to transplantable biological tissues. At least the surfaces of implants are made of biocompatible materials. Such materials include classes of such plastics and/or metals that are known in the medical arts for their biocompatible properties. Implantable devices can be used to replace a missing bodily function, enhance an existing function, or otherwise mediate a function. For example, implants exist for replacement or support of bones and teeth; cardiac rhythm management, drug delivery, cosmetic enhancement, and repair of organs or tissues.

Particular challenges exist in the design and use of implantable devices. For example, many classes of implantable devices need to be small and light weight so that they are minimally invasive. They must also be long lasting to help avoid the need for repeat surgical procedures to service or replace an implanted device.

The challenges inherent in the design of implantable devices having integrated electronics components are particularly onerous. For example, such devices must have proper electrical insulation and grounding to reduce the risk of shorting causing device failure or shock to patients. They must have low power requirements and long battery life for operational longevity. In applications such as cardiac rhythm management, it is critical that devices operate as reliably and safely as possible.

To address at least some of the aforementioned concerns, some implantable devices have been designed using molded plastics. For example, thermoplastics can be injection molded to provide lightweight devices having integrated electronics components. The plastic serves not only to provide a highly configurable shape, but also electrical insulation and hermetic sealing around integrated electronics components. Some applications are seen in US Patent Pub. No. 20090017700.

There are particular challenges to integrating electrical other components into molded plastics. The components must be precisely placed in the body of the device and relative to electrical interconnects or other parts in the body. Shapes must be precisely rendered in the molded form. Injection molding is a favored technique for forming body portions of implantable devices, but there are other forms of molding plastics, such as blow molding, thermoforming, reaction injection molding, compression molding, transfer molding, film insert molding, rotational molding, extrusion molding. Injection molding will generally be used hereafter as a representative example herein.

The very nature of the injection molding process, as well as other molding processes, is at odds with the objectives of precision placement and shaping of components. This is because injection molding involves the injection of pressurized, flowing materials into the cavity of a mold. The force of the flowing material can dislodge components that are positioned in the mold cavity. The flowing material may not completely surround components. Or the materials may not form to dimensions and shapes that meet design specifications and tolerances. These problems can result can result in components being out-of-position, incorrectly formed, or surrounded by air gaps, any of which can cause the implantable device to short circuit or otherwise to function improperly. For example, CRM devices have a "header" portion that includes an antenna for sending or receiving data signals wirelessly to or from a patient's body. An example CRM device 1 implanted into the chest of patient is schematically shown in FIG. 1. A closer schematic view of CRM 1 is shown in FIG. 2. The header 12 also has electrical conductive paths and couplings for connecting to the pulse generator module. The header 12 also has electrical connectors for receiving electrical one or more electrical leads, e.g., leads 14, 16, 18, 20, that connect to heart tissue to sense heart rhythms. In response to sensed rhythms, the header receives signals from the pulse generator 12 and passes them through the leads to stimulate heart tissue into a programmed rhythm. In one suitable design for an antenna 24, as generally indicated, in, for example, FIG. 3, the antenna is a conductive filament disposed along the peripheral sides of the body of the header. Maintaining the position of the antenna in the mold cavity in an injection molding process has proven to be challenging given the length of the filament and its alignment along multiple sides of a small-scale device.

Furthermore, a filament antenna for use in an implantable device typically has a small diameter, a relatively flat cross-sectional profile, or both, that is vulnerable to damage during the relatively high pressure or turbulence of an injection molding process. Thus, a substantial need exists to secure and protect fragile implantable device components, such as antennae, during molding or other fabrication processes.

Given the foregoing exemplary needs and considerations, an ever present need exists for improved molded implantable devices.

SUMMARY

The innovations and related principles described herein overcome the foregoing and other needs of the prior art. For example, the following describes injection molding systems, injection moldable articles and other subcomponents that can be combined to form an implantable medical device.

As noted, one aspect of such innovative subject matter relates to implantable medical devices. Some described implantable medical devices include a first molded construct and a second molded construct overlying the first molded construct at an interface.

As used herein, "construct" means a physical thing that is built or formed.

The first and the second molded constructs can each include a plastic material. A component having a selected configuration can be retained, at least in part, by the first molded construct. The component can have at least one section disposed at the interface between the first molded construct and the second molded construct so that the component contacts one or both constructs at the interface.

In some instances, the component is or includes an antenna extending generally peripherally of the first molded construct. The component can be disposed at least partially within the first molded construct.

In some instances, least a portion of the component can be disposed in an elongate path along the interface boundary surface of the first molded construct. For example, the portion of the component can include a first portion of the component disposed in a channel formed in the first molded construct and a second portion extending outwardly of the channel. The second molded construct can overlie the second portion of the component extending outwardly of the channel. In some instances, the second molded construct overlies the first construct and the portion of the component disposed along the elongate path so as to surround that portion of the component and hermetically seal it.

In some embodiments, the component can include at least one antenna or a conductor element that is exposed at a surface of the device, free of material of the first construct and the second construct. For example, the component can include a first antenna or a first conductor element disposed along the elongate path and a second antenna or a second conductor element that is exposed at a surface of the device, free of material of the first construct and second construct.

The component can include or be an antenna disposed along a path generally following about 25% or more of an outer perimeter of the device. For example, the antenna can be disposed along a path generally following about 50% or more of the outer perimeter of the device, such as about 75% or more of the outer perimeter of the device.

The device can also include at least a portion of a corresponding passage configured to receive an electrical lead suitable for use with an implantable medical device. In some embodiments, the device can have from 2 to 6 of said portions of corresponding passages, such as three or more of said portions of corresponding passages. Such a portion of the corresponding passage can be further configured to allow the lead to communicate with electrical circuitry for the device. The electrical circuitry can include a pulse generator for a cardiac rhythm management or a pain management device.

For example, the device can include or be a header for an implantable cardiac rhythm management or an implantable pain management device. For example, such a header for an implantable device can be configured to receive an end of a lead configured to communicate signals from the end of the lead to another end of the lead being configured to contact a patient's tissue.

The first and second molded constructs can include a plastic selected from one or more of a biocompatible resin suitable for long-term in vivo use. For example, the resin can include a thermoplastic polyurethane, such as, for example, an aliphatic polyurethane, an aromatic polyurethane, a polycarbonate polyurethane, an aromatic polyether polyurethane, an aromatic polyester polyurethane, an aliphatic polyester polyurethane, an aliphatic polyether polyurethane or a combination thereof.

In some embodiments, at least a region of the first molded construct is fusion-bonded to a corresponding region of the second molded construct.

Other inventive aspects are also disclosed. For example, methods of making implantable medical devices are disclosed. At least a portion of a first mold cavity configured to form at least a first molded construct of an implantable medical device can be provided. The mold cavity can have a receiving feature configured to hold or receive a component during an overmolding process. A moldable plastic material can be introduced into the first mold cavity. The plastic material can be capable of taking the shape of the mold cavity to form a first molded construct of the device having a shape corresponding to the respective portion of the first mold cavity. A component can be positioned in the respective portion of the first mold cavity before the introduction of moldable plastic material, or on the molded first construct following introduction of the moldable plastic material, so that at least one segment of the component is securely disposed at a surface of the formed first molded construct. At least a portion of a second mold cavity configured to form at least a portion of an implantable medical device can be provided. The formed first molded construct with the positioned component can be placed into the respective portion of the second mold cavity. A moldable plastic material capable of taking the shape of the second mold cavity can be introduced into the second mold cavity to form a second molded construct of the device having a shape corresponding to a shape of the second mold cavity. The first and second molded constructs can be moldably fused together at an interface therebetween. The component can be disposed at the interface of the first molded construct and the second molded construct.

The component can be disposed in the first mold cavity before the moldable plastic is introduced to the first mold cavity. For example, the component can be securely positioned adjacent a surface of the first molded construct after forming of the first molded construct and before forming the second molded construct. One or both of the first and second molded constructs can be formed using an injection molding technique.

According still other inventive aspects, alternative embodiments of an implantable medical device are disclosed. For example, some disclosed devices have a first molded construct defining one or more peripherally-positioned receptacle features configured to support an elongate component is disclosed. A surface area of the first molded construct is less than about 60% of a projected plan area of the first molded construct. An elongate component extends longitudinally of one of the receptacle features. A second molded construct overlies the first molded construct and at least a portion of the elongate component.

The surface area of the first molded construct can be less than about 30% of the projected plan area of the first molded construct.

In some embodiments, the first molded construct can have a skeletal frame configured to retain the elongate component during overmolding of the second molded construct. The skeletal frame can define at least one cantilevered member configured to retain a corresponding portion of the elongate component. The cantilevered member can have a support element configured to engage a corresponding support element of a molding die configured to form the second molded construct. In some instances, the support element has a boss. Some such bosses define an aperture extending through the boss, such that the support element of the molding die configured to form the second molded construct can extend through the boss and thereby support the cantilevered member of the skeletal frame.

A portion of the first molded construct and a portion of the second molded construct can be fusion bonded to each other.

These and other embodiments are described in more detail in the following detailed descriptions and the figures.

The foregoing is not intended to be an exhaustive list of embodiments and features of the inventive subject matter. Persons skilled in the art are capable of appreciating other embodiments and features from the following detailed description in conjunction with the drawings.

BRIEF DESCRIPTION OF THE DRAWINGS

The following figures show embodiments according to the inventive subject matter, unless noted as showing prior art.

FIG. 6 is an isolated view of the first molded construct of the device shown in FIG. 3, the view being a front right side perspective.

FIGS. 7A and 7B show an alternative embodiment similar to the device of FIG. 6., the views respectively being left and right front perspective views.

DETAILED DESCRIPTION

Figure 1:
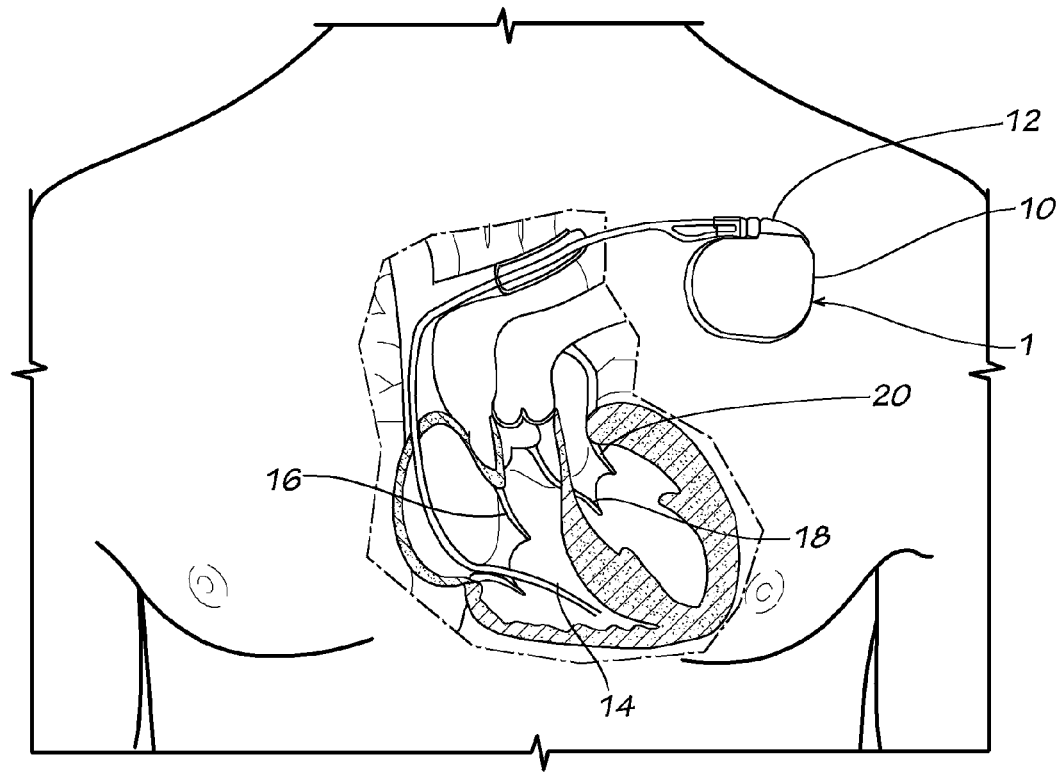
FIG. 1 shows an example of a prior art implantable medical device in place in a patient's body.
Figure 2:
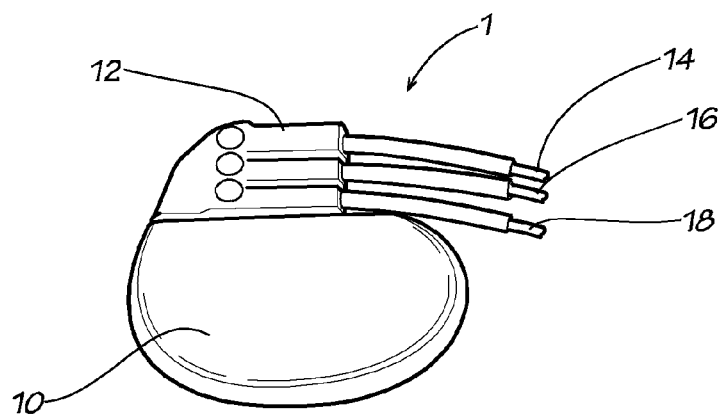
FIG. 2 shows an example of a prior art implantable cardiac rhythm management device consisting of a pulse generator and header assembled together.
Figure 3:
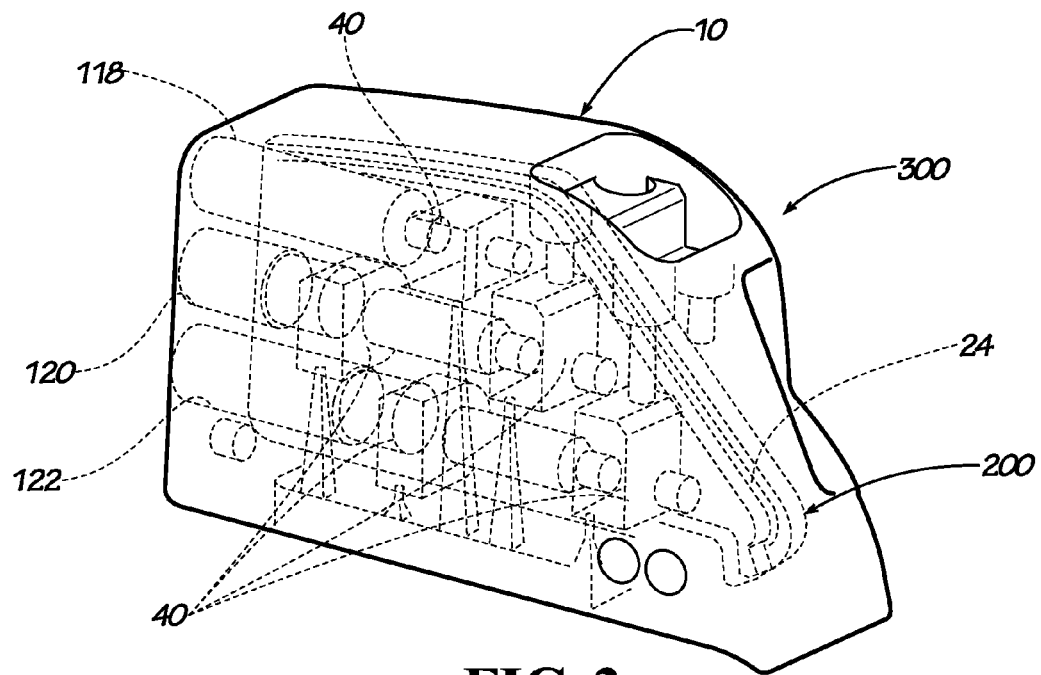
FIG. 3 shows a front left perspective view of a molded header device consisting of a first molded construct supporting a component and an over-molded second construct.
Figure 4:
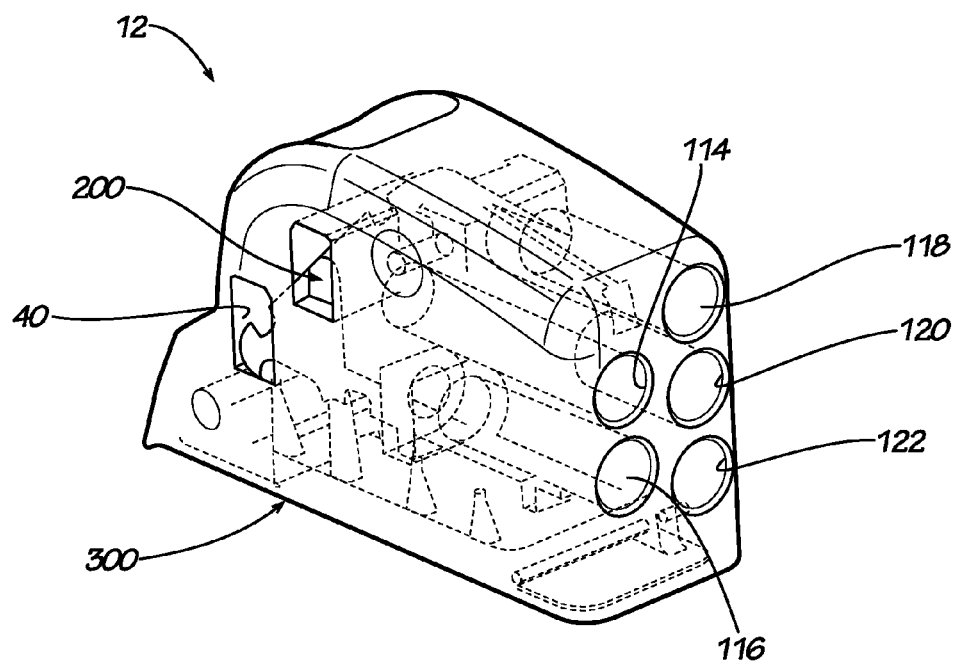
FIG. 4 shows a perspective view from the rear of the right side of the device shown in FIG. 3.
Figure 5:
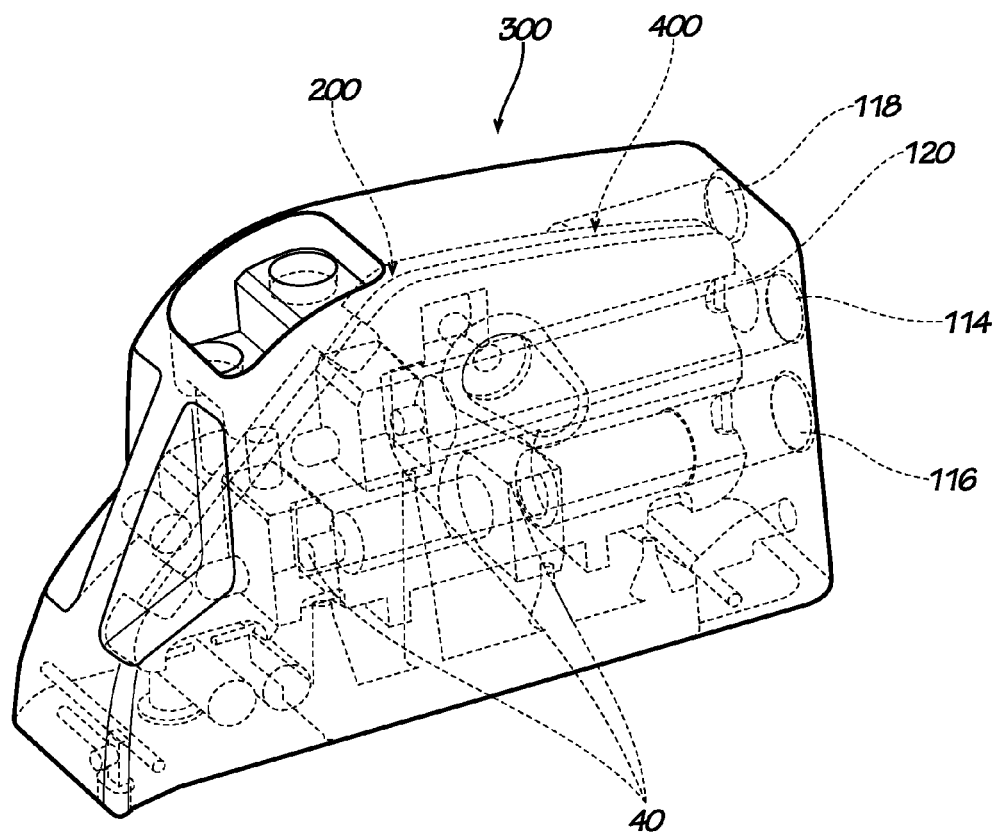
FIG. 5 shows a perspective view from the front of the right side of the device shown in FIG. 3.

Representative embodiments according to the inventive subject matter are shown in FIGS. 1-18, wherein the same or generally similar features share common reference numerals.

The inventive subject matter generally relates to implantable medical devices. It particularly relates to implantable devices made of molded plastics and having integrated electronics components, such as RF antennae, conductive elements, functional devices (e.g., resistors, semiconductor chips, RF devices, etc.), and optical guides (e.g., optical fiber for carrying signals used by electrical devices). The inventive subject matter is particularly suited for use with implantable devices for Cardiac Rhythm Management (CRM). Accordingly, such devices will be used herein to illustrate principles of the inventive subject matter. However, persons skilled in the art will appreciate from the teachings herein that the inventive subject matter may be readily adapted to other kinds of implantable devices, such as implantable pain management devices.

The basic components of a CRM implantable device 1 are a battery-powered pulse generator 10 and a header 12. The pulse generator and header are typically independent modules that assemble together. The term "implantable device," as used herein, is intended to cover both an assembly of such modules or the modules standing alone.

The pulse generator has an onboard microprocessor and memory programmed for sensing conditions and responding with appropriate electrical stimuli. The pulse generator's components are typically enclosed in a small metal housing. Other components of the pulse generator may be an input sense amplifier, a sensor, a transceiver circuit to allow monitoring and programming via an external telemetry loop, a pulse generator, and a power supply, all under the power of one or more onboard batteries. The sensor in the CRM is usually a microelectromechanical system (MEMS) accelerometer. Such features are well known in the art and are not specifically described or illustrated herein.

The header 12 supports one or more electrical leads, e.g., leads 14, 16, 18, 20, which can electrically couple to target tissue, as indicated in FIG. 1. Typically, the header defines a recessed feature, such as, for example, a socket or a receptacle (also referred to as a "lead bore") 114, 116, 118, 120, 122 (FIG. 4), corresponding to each respective lead. One or more of the leads and a corresponding one or more of the receptacles can be matingly engageable with each other such that the respective leads and receptacles may removably and securely plugin together, so as to form an operative electrical coupling therebetween.

The header is typically made of a molded, dielectric material to insulate electrical components from each other. Various moldable plastics may have such properties and may be used to form the body of the header. The header contains electrical connections and circuits for communicating with the pulse generator. Also, it typically includes an antenna for transmitting or receiving signals to or from the patient's body. For example, data about the condition of the implantable device or the patient may be transmitted via the antenna 24 to a remote computer for analysis. Similarly, a remote computer may transmit data for programming the pulse generator to the pulse generator's memory via the antenna.

The leads that are coupled to header are insulated, flexible wires (e.g., flat wires, small diameter wires) that conduct electrical signals to the heart from the puke generator. As generally illustrated in FIG. 1, one end of the lead is configured to electrically connect to the CRM device via circuits in the header and the puke generator in communication with the lead receptacles, and the other end is configured with ara electrode to electrically connect to tissue in a patient's body. In one possible CRM protocol, one end of a lead is attached to the puke generator and the electrode end of the lead is positioned in the atrium (the upper chamber of the heart) or in the right ventricle (the lower chamber of the heart). The leads thereby can deliver electrical signals to the tissue. The leads may act as a sensor, relaying signals from about the condition of the heart or other tissue to device components, such as the memory and microprocessor. An implantable device may be configured to support any number of leads. In Typical CRM applications, there would be 3 or more lead receptacles for connecting three or more leads. In some embodiments, there may be enough receptacles to connect from 2 to 6 leads. The embodiments shown in FIGS. 3-14 have 5 receptacles.

As noted in the Background section, there are significant challenges to making a molded implantable device with precisely formed and arranged features. For example the molding of an integrated antenna is subject to challenges. The inventive subject matter overcomes the challenges by providing a staged molding process. In a first stage, the component that is to be integrated is fixed in place in or on a first molded construct 200. The component may be over-molded in place. Alternatively, the component may be arranged on a premolded part having means to receive and secure the component.

In a second molding stage, the assembly of first molded construct 200 and component 24 are placed in a mold that is configured to form a second molded construct 300 to complete or augment the form of the first molded construct. The process results in an implantable medical device (which may require assembly of further components), or module thereof, where there is a first molded construct 200 and a second molded construct 300 that can be fusion bonded to the first molded construct at an interface 400.

FIGS. 3-14 detail one possible embodiment of an implantable header assembly 12 (or simply "header") forming a module for use with another module of an implantable medical device. In this embodiment, the header consists of an inner core or first molded construct 200 formed of a molded plastic. Representative classes of moldable materials include medical grade urethanes, silicones, and any other biocompatible material suitable for injection molding devices for in vivo applications, such as, for example, implantable grade thermoplastics and thermosets. Representative thermoplastic polyurethanes (TPUs), which may be suitable, include those sold under the brand names Tecoflex®, Tecothane®, Carbothane®, Tecoplast® and Tecophilic®, which are available from Lubrizol Advanced Materials, Inc., Wilmington Mass., USA. Tecothane material TT1075D-M may be used, for example, in applications demanding electrically insulative properties. Tecothane is an aromatic polyether-based polyurethane). Carbothane is an aliphatic polycarbonate-based polyurethane, Tecophilic is high moisture absorption aliphatic polyether-based polyurethane, and Tecoplast is an aromatic polyether-based polyurethane. [Information pertaining to these and other suitable materials may be available from http://www.lubrizol.com/TwoColumn.aspx?id=40599&terms=tecothane.]

The component may be completely over-molded with molded material of the first molded construct and/or the second molded construct so no surface is exposed. Or it may have at least one section disposed between the first molded construct and the second molded construct so that the electronic component is fusion bonded to both constructs at a molded interface of the materials. In either case, the component 24 may reside entirely or almost entirely at the surface of the first molded construct (exposed or thinly covered with molding material). Or it may have a section exposed at the surface and a section that is buried deeper into the first molded construct.

The embodiment shown in FIGS. 3-13 includes a component 24 that is molded into the header 12. In this example of the inventive subject matter, which will be used as a representative example, the component is an electronics component in the nature of a single-filament antenna. As seen in the Figures, the component 24 generally follows elongate paths corresponding to each side of the header. The paths are joined at angles generally corresponding to the angular relationships between adjoining sides of the implantable device 1. The antenna is disposed along the surface of the first molded construct, and that surface becomes fusion bonded to the second molded construct. In some embodiments, one or more exposed sections 24A of the component may be provided in device 1. By surrounding the component, or some portion of it, with the material of the first molded construct and/or the second construct, a hermetic sealing of the component, or a desired portion of it, may be achieved.

A wall thickness of the first molded construct can be selected to provide the corresponding wall of the first molded construct with any of a variety of corresponding physical characteristics, e.g., a relatively thicker wall of the first construct is relatively stiffer than a thinner wall, and a relatively thicker wall tends to melt less than a relatively thinner wall during overmolding of the second molded construct, leading to a corresponding lesser degree of fusion bonding between the first molded construct and the second molded construct for a thicker wall In practice, a wall thickness of the first molded construct can range from about 0.030 inch to about 0.090 inch. A wall thickness of about 0.030 inch can be quite meltable during overmolding of the second construct, e.g., up to about 50 percent of the material forming a wall having a thickness of about 0.030 inch can melt during overmolding, providing a high degree of fusion bonding between the first molded construct and the second molded construct. A wall thickness of about 0.090 inch can be relatively unmeltable, e.g., about 5 percent, or less, of the material forming a wall having a thickness of about 0.090 inch can melt during overmolding, providing relatively lower fusion bonding between the first molded construct and the second molded construct.

As seen in FIG. 7, to better retain the component 24 during the molding of the second molded construct 300, a receptacle 26 (e.g., a groove, slot, tube, aperture, channel, etc.) may be formed in the first molded construct 200. The second molded construct over-molds some or all of the electronics component in the receptacle. In some embodiments, the receptacle is formed in the molding of the first molded construct and the component is placed in the formed receptacle before the over-molding step that forms the second construct, so as to anchor (e.g., retain) the component 24 in a desired configuration and position during over-molding. In such case, there would be no initial fusing of the first molded construct to the component. However, depending on molding conditions, the surface of the first molded construct could melt and fusion bond to the component during the over-molding process forming the second molded construct.

The placement of antenna 24 around the periphery of implantable device 1 facilitates transmission and reception of signals. In some embodiments, an antenna or other electronics component is disposed along a path generally following about 25% or more of the outer perimeter or periphery of the molded plastic device, based on a circumferential-type path around a major axis of a circular or non-circular object. In other embodiments, the path follows about 50% or more of the outer perimeter. In still other embodiments, the path follows about 75% or more of the outer perimeter.

In some applications, such as antenna applications, the path is generally elongate and continuous in nature, i.e., the path is a substantially linear path or a substantially continuous, non-complex curvilinear path extending over a major surface(s) portion of the first and/or second molded construct. For example, looking at the Figures, header 12 has four sides of varying lengths. The sides connect at varying angles. Each side may be considered a major surface portion. The antenna is molded into the first molded construct 200 at about the outer perimeter of the device so that it follows each side in a generally linear path. Except for a small gap 28 separating the ends 24B and 24C of the antenna, the antenna follows the entire perimeter of the first molded construct, i.e., it follows more than about 90% or more of the outer perimeter of the first molded construct. The second molded construct 300 is formed over the first molded construct 200 to generally mimic the shape of the first molded construct so that the antenna is still relatively close to the surface of the overall header device.

Accordingly, the antenna follows the outer perimeter of the second molded construct 300, and the overall header device 1, in the same manner as it does the first molded construct 200. The antenna defines a generally elongate path along any given side. The path is also continuous given the circumferential nature of the path around the device.

The antenna may be made of various materials that are well known in the art for transmitting or receiving electromagnetic radiation, particularly for in vivo applications. For example, antennas may be based on alloys of platinum, titanium, Stainless steel, gold, or other metal alloys suitable for in vivo uses. An antenna may also be based on non-metallic filaments of carbon nanotubes and other suitable, conductive non-metals, as are known.

In the embodiment shown, the antenna is covered almost entirely in insulative plastic of the first and second molded constructs 200, 300, except for one or more exposed areas 24A,B, C.

In the embodiment shown, there are five small, notched sections 24A spaced along the periphery. The notches leave short sections of the filament exposed. The five sections extend out of sidewalls of the notches, bridging across the sidewalls without touching the bottom base of the notches. A sixth notch or gap 28 contains the ends 24B, 24C of antenna filament 24. The exposed areas may be used to make electrical interconnections, e.g., that couple the antenna to other electrical circuitry in the header and/or the pulse generator. For example, each portion of the filament exposed at the notches 24A can be electrically coupled to one or more corresponding leads. The ends of the filament 24B, 24C can be coupled (e.g., by welding) to one or more electrical circuits configured to provide the functionality described herein. For example, after the molding process described below, wires may be welded, soldered or mechanically fastened to the ends of the antenna during the assembly to the pulse generator module.

The header device 12 may also define one or more features (e.g., recesses, notches, slots, grooves, holes, rails or snap fittings) configured to connect to another device or component, such as a pulse generator. For example, in the embodiment shown, a plurality of recesses 40 are provided for receiving set screw blocks or other hardware for coupling the pulse generator to circuitry components and/or the header. Alternatively, the hardware components may be molded in place with the molding of the first or second molded constructs.

After the first and second constructs are molded to form a subassembly, either with or without other hardware components, it can be assembled with other components and subassemblies into a functional device. For example, one or more electrical leads can be coupled to the electrical component, as described above.

Figure 15:
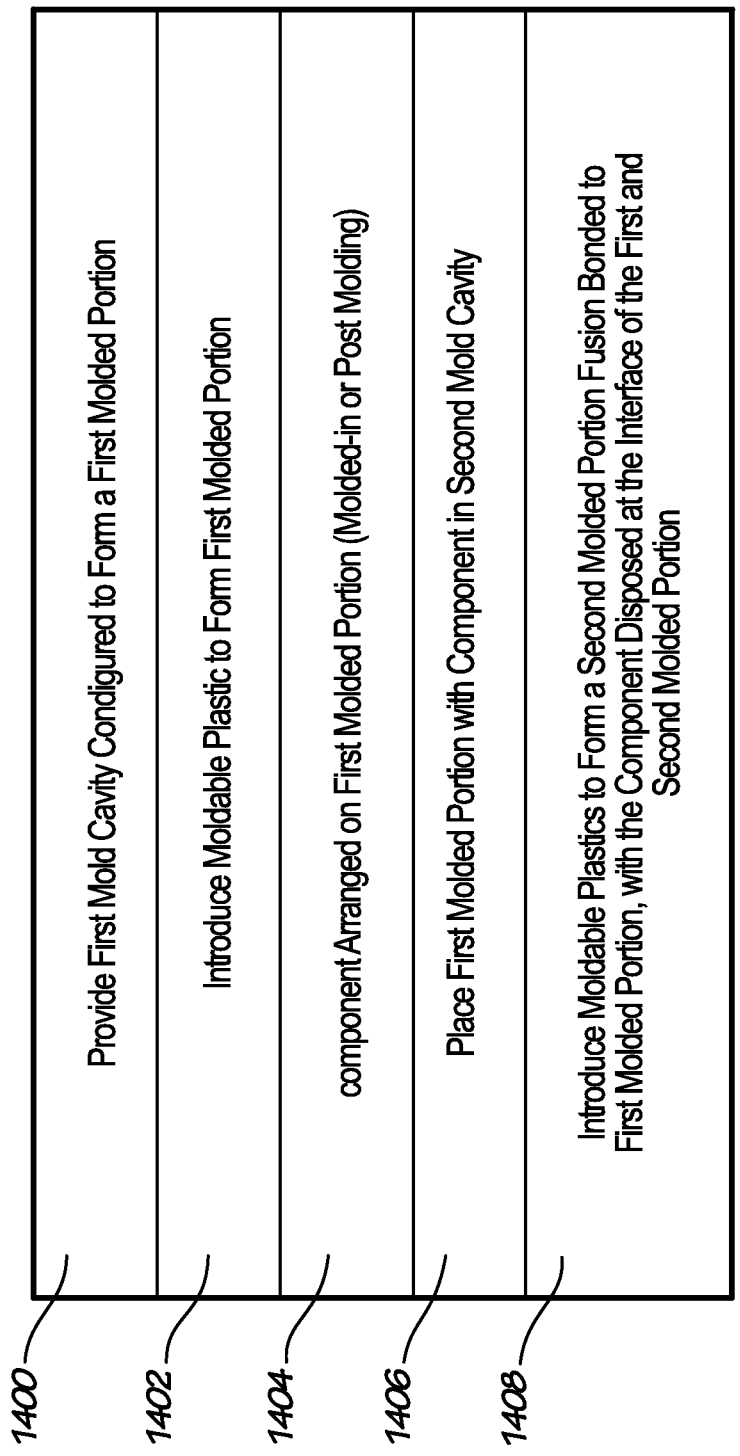
FIG. 15 is a block diagram of steps used in a representative embodiment of a molding process for forming an implantable medical device.

FIGS. 8-13 show example tools for molding an implantable device like the one shown in FIGS. 3-7. FIG. 15 is a flow chart illustrating one possible set of molding steps consistent with the teachings herein. Step 1400 includes at least providing a first mold cavity configured to form at least a first molded construct, which can be coupled to one or more other constructs to form an implantable medical device, the mold cavity having an area for holding or receiving an electronics component, in this case antenna 24. The mold cavity may be defined by two or more complementary tooling parts 900A and 900B. Each tooling part represents a portion of the internal volume of the overall mold cavity. The parts combine to define an internal volume representing the shape of the article to be molded.

Step 1402 includes at least introducing into the mold cavity or a portion thereof a moldable plastic material capable of taking the shape of the mold cavity and forming a first molded construct, a subcomponent of the device, to the shape of the first mold cavity. Injection molding, which involves introduction of a flowing plastic material, under pressure, into the mold cavity, is one suitable molding technique for forming small-scale implantable devices, such as CRM devices.

Step 1404 includes at least arranging a component, e.g., an electronics component such as antenna 24, in a portion of a mold cavity before the injection or other introduction of moldable material. Alternatively, the component may be securely arranged in a groove, channel passage or other recess formed into the first molded construct and configured to retain the component, as described above relative to the embodiment shown in FIG. 7.

Figure 8:
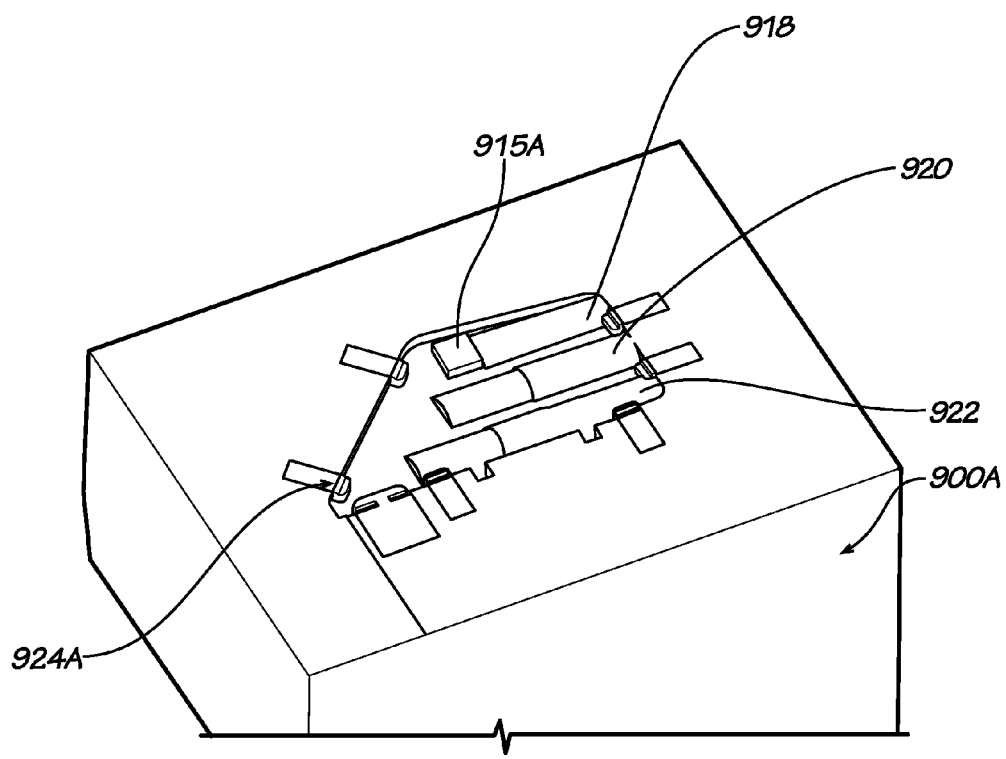
FIG. 8 shows a part of a molding tool used to mold the first molded construct of FIG. 6.
Figure 9:
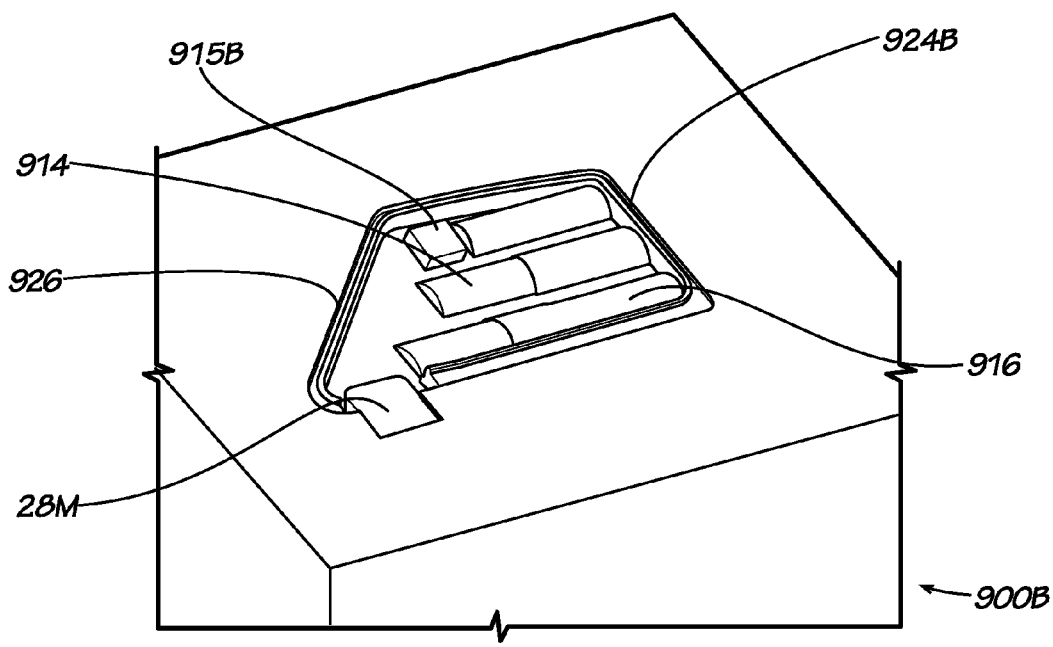
FIG. 9 shows an opposite part of the molding tool used to mold the first molded construct of FIG. 6.
Figure 10:
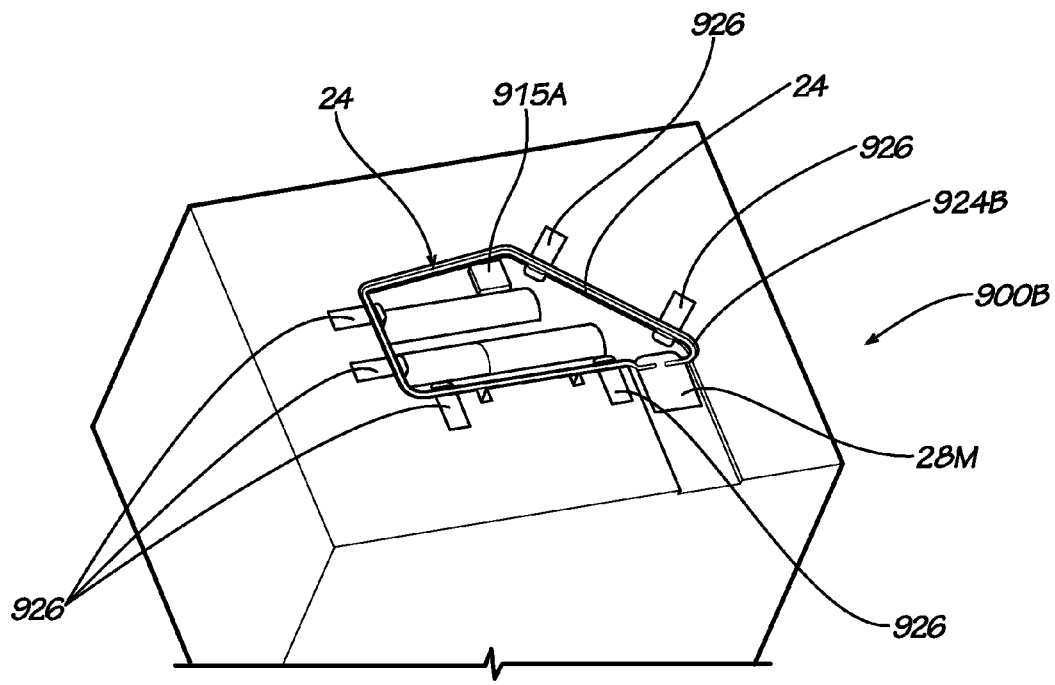
FIG. 10 shows the part of FIG. 9 with a component in place.
Figure 11:
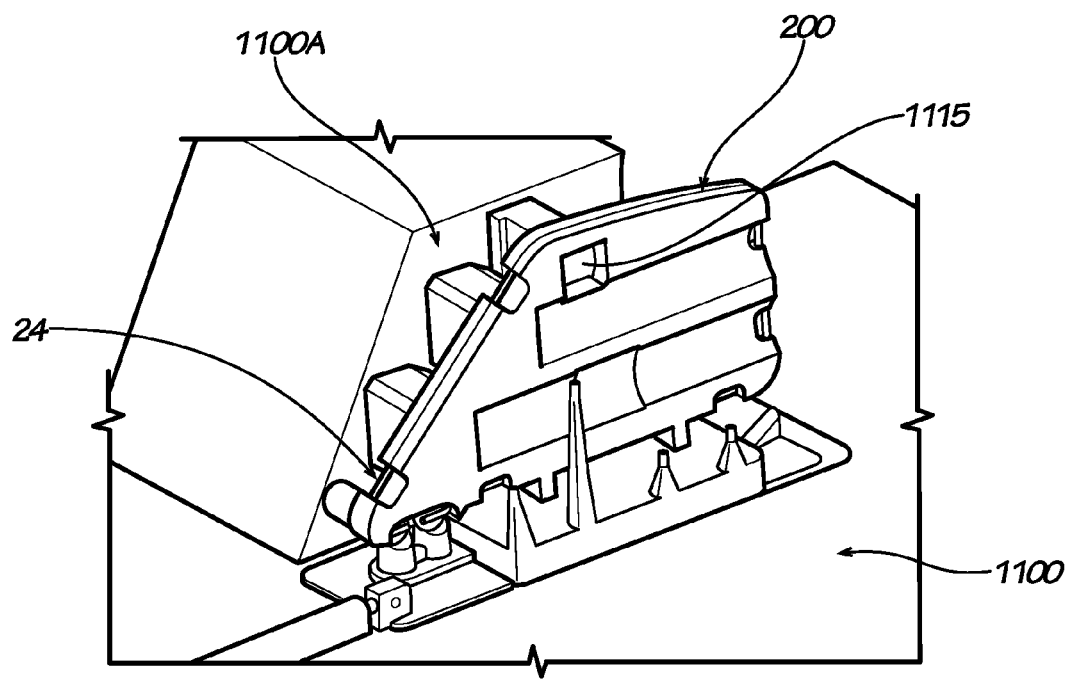
FIG. 11 shows the first molded construct with a molded-in component in part of a second molding tool for molding an over-molded second construct, the view being a front right perspective view of the first molded construct.

In the embodiment shown in FIGS. 8-10, parts 900A,B have associated retention means, such as fixed or removable clips 926, or grooves 924A,B, for arranging and securing the antenna in place during molding. FIG. 9 shows mold cavity 900B before antenna 24 is in place; FIG. 10 shows mold cavity 900B after antenna 24 has been placed in groove 924B. Whether the component is molded into the first molded construct or securely arranged on it afterwards, the result is that the component has at least one section that is securely disposed at the surface of the first molded construct. The component is securely disposed if it will stay in place during the over-molding or co-molding of the second molded construct.

The component is at the surface if it is on the surface or slightly below the surface. For example, if a part has a dimensional thickness of a given value, a component at a surface distance within 25% of the value would generally be considered at the surface. However, the inventive subject matter is not intended to layout strict formulas and substitute for common sense and judgment among persons skilled in the art in reasonably assessing if something is at the surface of something else.

Figure 12:
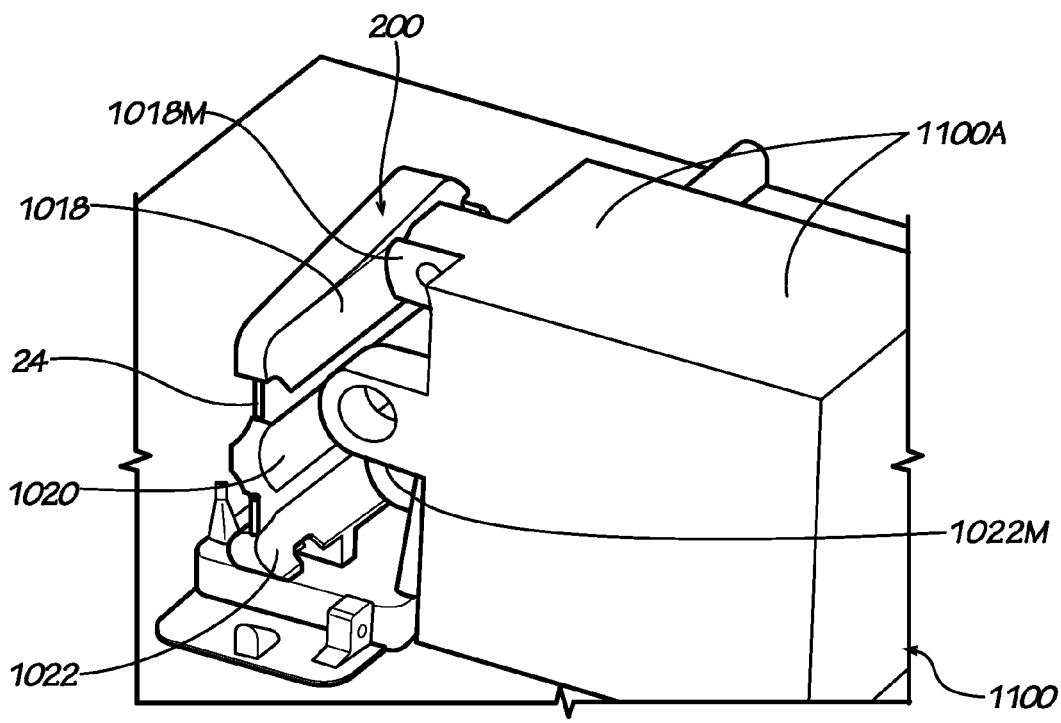
FIG. 12 shows a rear perspective view of the right side of the first molded construct and molding tool part shown in FIG. 11.
Figure 13:
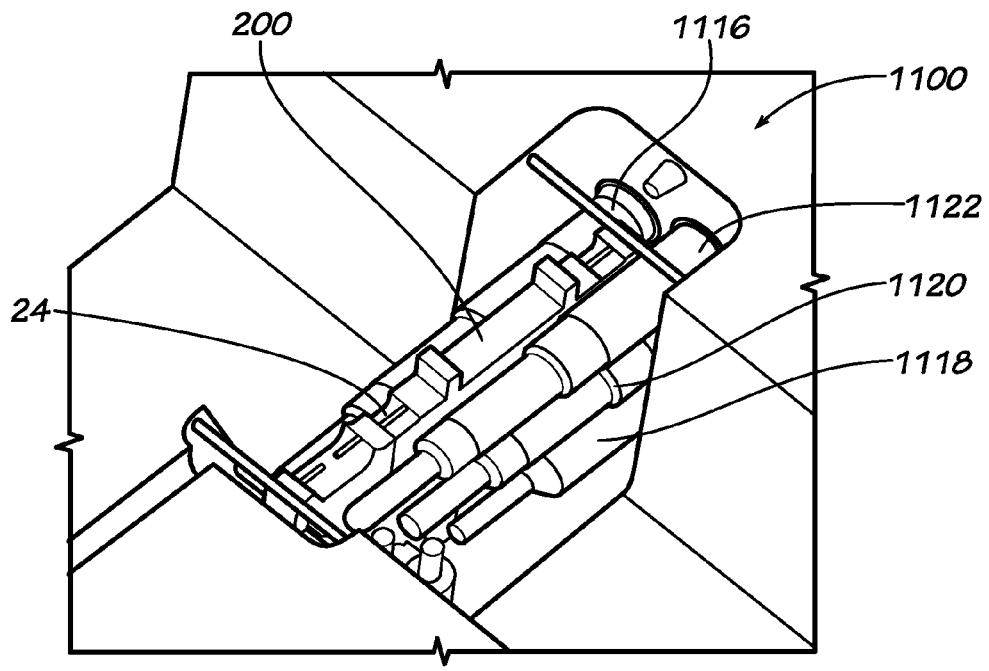
FIG. 13 shows a bottom perspective view of the first molded construct in a molding cavity configured to mold an over-molded second construct around the first molded construct so as to produce the unitary molded device of FIG. 3.
Figure 14:
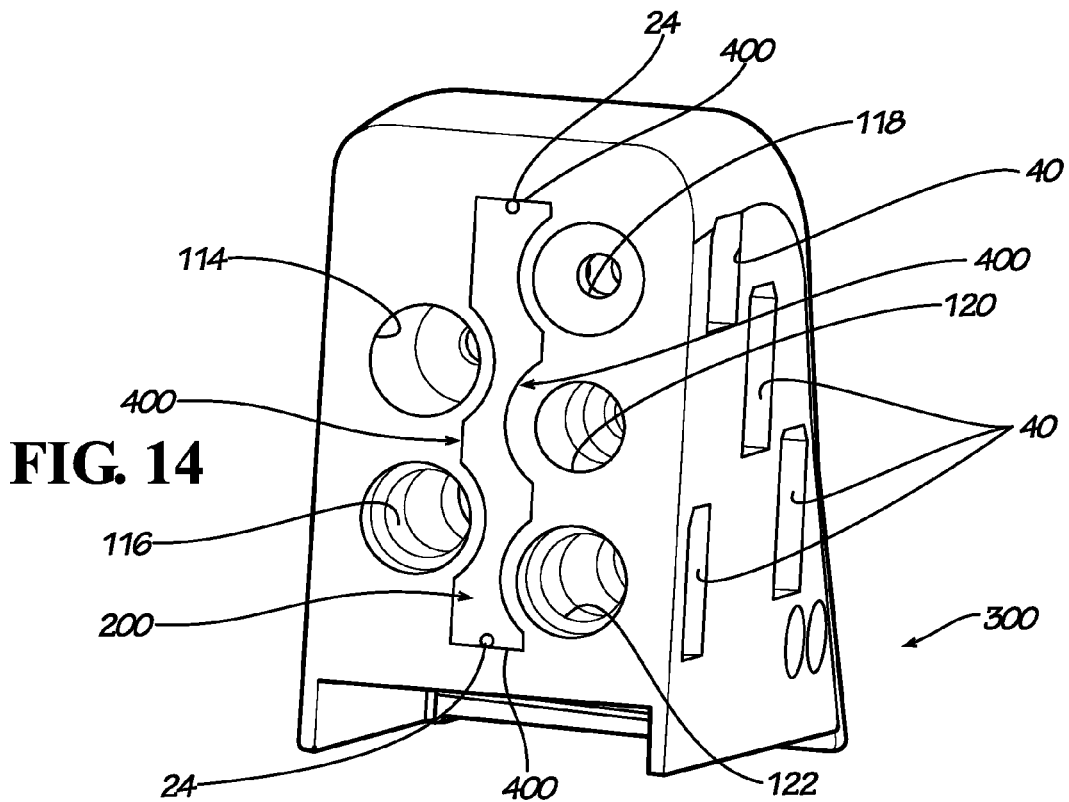
FIG. 14 shows a representative sectional view of the device of FIG. 3.

Step 1406 includes at least providing a second mold cavity configured to form at least a portion of an implantable medical device. Here also, the molding tool 1100 may be in two or more parts that combine to define a molded article. The first molded construct 200, with a secured, arranged component 24, is placed in the second mold cavity or portion thereof, as shown in FIGS. 12 and 13. Step 1408 includes at least introducing into the second mold cavity a moldable plastic material capable of taking the shape of the second mold cavity and forming a second molded construct, a subcomponent of the device, to the shape of the second mold cavity, the first and second constructs being fusion bonded together at an interface, wherein the electronics component is disposed at the interface of the first molded section and the second molded section. FIG. 14 is a section of device 1, shown in FIGS. 3-5, generally illustrating how the first molded construct 200 is completely over-molded with the material of the second molded construct 300 so as to define an interface boundary 400. It can be seen that component 24 is at the interface. The illustrations also generally represent that the component can be over-molded with material from the first molded construct and/or the second molded construct.

In the embodiment shown, the header includes a plurality of molded-in receptacles or other coupling means for receiving or otherwise connecting to the pulse generator or to other components. For example, the receptacle may be configured to house metal set-screw blocks 40. The antenna may be electrical isolated from these components; it does not necessarily extend or connect to the receptacles or the components placed in them. Advantageously the placement of one or more components in the first molded construct allows for precise separation of such components from other components that are disposed in the second construct. This is because the first component(s) are already fixed in place before they are introduced into the second mold or subsequent molding cavity and they will not move to detrimentally relative separations.

Looking in more detail at the mold tools, mold cavity portions 900A,B have shaped features, e.g., longitudinal disposed half-cylinders 914, 916, 918, 920, and 922 that form complementary shapes in the first molded construct that facilitate the placement and alignment of the first molded construct in the cavity of the molding tools for the second molded construct. For example, features 918, 920, and 922 form corresponding shapes 1018, 1020, and 1022 in the first molded construct. As seen in FIG. 12, those shapes align with molding tool features 1018M, 1020M, and 1022M in one part of mold tooling 1100. Molding tool features 1018M, 1020M, and 1022M align and facilitate placement of tooling shapes 1116, 1118, 1120, 1122 (FIG. 13) that define passages 116 and 118, 120, and 122 in the second molded construct 300.

The mold tooling may also include fixed or removable blanks, e.g., 915A,B or 28M, for defining voids or other shapes in the molded item. For example, the shapes 915A,B match-up in the mold and define a square void 115 in molded construct 200 that is used in aligning and handling that construct in the second mold cavity part 1100A, FIG. 11.

Once a mold cavity is ready, the moldable material is injected or otherwise introduced into the cavity and it takes the shape of the mold cavity and molds to the antenna. Once the first molded construct is set, it is removed from the first molding tool and arranged in a second molding tool that for the second molded construct. In the embodiment shown, the second molded construct 300 substantially completely over-molds the first molded construct 200. In other words, the first molded construct may serve as a core element for the second molded construct. The second mold cavity therefore substantially defines the shape of the header, as well as various internal features. Once the first molded construct is in place in the mold the moldable materials is typically injected under a suitable temperature (e.g., so the moldable material is suitably flowable) and a suitable pressure, or otherwise introduced into the mold cavity. Typical temperatures can range between about 250° F. and about 800° F., and typical pressures can range between about 200 pounds per square inch (psi) and about 35,000 psi. Once the material is set, which usually requires cooling, a unitary part consisting of the first and second molded constructs may be removed from the mold.

In another possible embodiment, noted above, the component is not prearranged in the mold cavity during the molding of the first molded construct. However, the mold cavity is configured to define a groove or other means for securely receiving the component. Once the first molded construct has set, the component may be placed into the groove or other receiving means. This assembly is then placed into a second mold for the second molded construct, and molding proceeds, as described above. No matter how the molding of the component proceeds, the end result after the molding of the second molded construct is the same.

Notably, there may be more than two iterations of molding. For example, there may be additional over-molding steps to create distinct portions of the device with one or more components in the overall end product of the moldings. Any given interfacing portions of molded materials may or may not have a component at the interface boundaries.

In contrast to the prior art, such as US Patent Pub. No. 20090017700, mentioned above, the over-molding process of the inventive subject matter does not need to involve positioning of any additional conductive elements into the mold before or during the molding. The only functional conductive element in the molded material may be the antenna, which is embedded in the core element. The molding process is simplified by eliminating all components from assembly in mold cavities, except where there may be an advantage, e.g., where a hermetic or electrically insulative sealing is needed, such as in the case of an antenna.

The moldable plastic used in the over-molding of the core element may be identical to that which is used to form the first molded construct or it may be different. During the over-molding, the structural shape of the first molded construct is entirely or substantially maintained; it becomes fusion bonded to the over-molding material without substantial shape change.

The elements intended for placement in the receptacles, passages or other channels may be inserted after the resulting first or second molding steps. For example, after the molding steps, electrical elements or fasteners for an implantable device may be placed into the channels formed in the molding steps using press fitting, adhesives, or heat-fusion bonding, for example.

Figure 16:
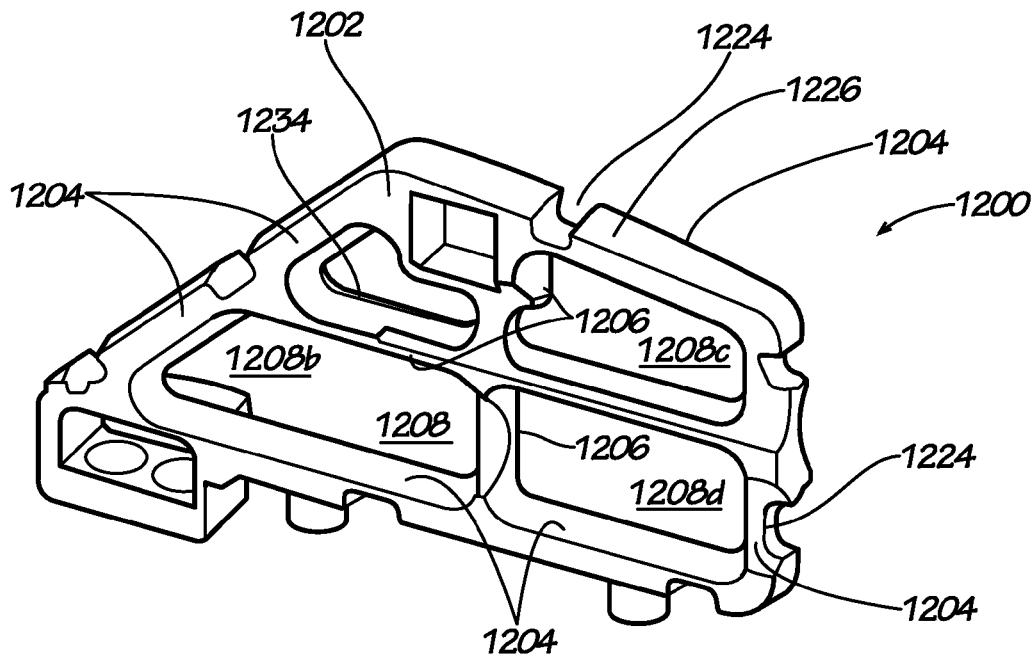
FIG. 16 shows an alternative embodiment of a first molded construct.

As shown in FIG. 16, a first molded construct 1200 can define one or more peripherally-positioned receptacle features 1224, 1226, similar to the construct 200, configured to support a component (e.g., antenna 24), such as during over-molding. The construct 1200 also defines a skeletal frame 1202 having a peripherally-extending wall 1204 and a plurality of struts 1206 spanning an interior region 1208 defined by the wall. The struts 1206 and wall 1204 define a truss-like structure having a plurality of apertures 1208*a*, 1208*b*, 1208*c*, 1208*d*.

The apertures 1208*a*, 1208*b*, 1208*c*, 1208*d* reduce the amount of surface area of the first construct 1200 in contact with the over-molded second construct (e.g., construct 300 in FIG. 3) allowing flowable material to flow past and/or fill one or more of the apertures during overmolding. The reduced surface area can reduce shear stresses between the first construct 1200 and the flowable material and can reduce overall heat transfer between the flowable material and first construct 1200 as compared to the construct 200 (FIG. 6). One or both of the reduced shear stress and reduced heat transfer can reduce deformation of the first construct 1200, and thus of the component it supports, during overmolding as compared to deformations experienced by the construct 200. In some embodiments, a surface area of the first molded component is less than about 30% of a projected plan area of the first molded component. In other embodiments, a surface area of the first molded component is less than about 60% of a projected plan area of the first molded construct. Such a construct is shown for example in FIG. 17. As used herein, projected plan area means the area lying within a projection of a physical article onto a plane.

It was discovered that, surprisingly, shear forces in the flowable material used to form the second molded construct do not necessarily require such an open skeletal frame for the first molded construct. Rather, it was discovered that such open frames for the first molded construct can, in some embodiments, allow the material used to form the second construct to more fully fill the mold (e.g., by redwing a volume fraction of trapped air, or other gasses, or other regions devoid of the flowable material), while reducing or eliminating movement of, for example, the antenna.

Figure 17:
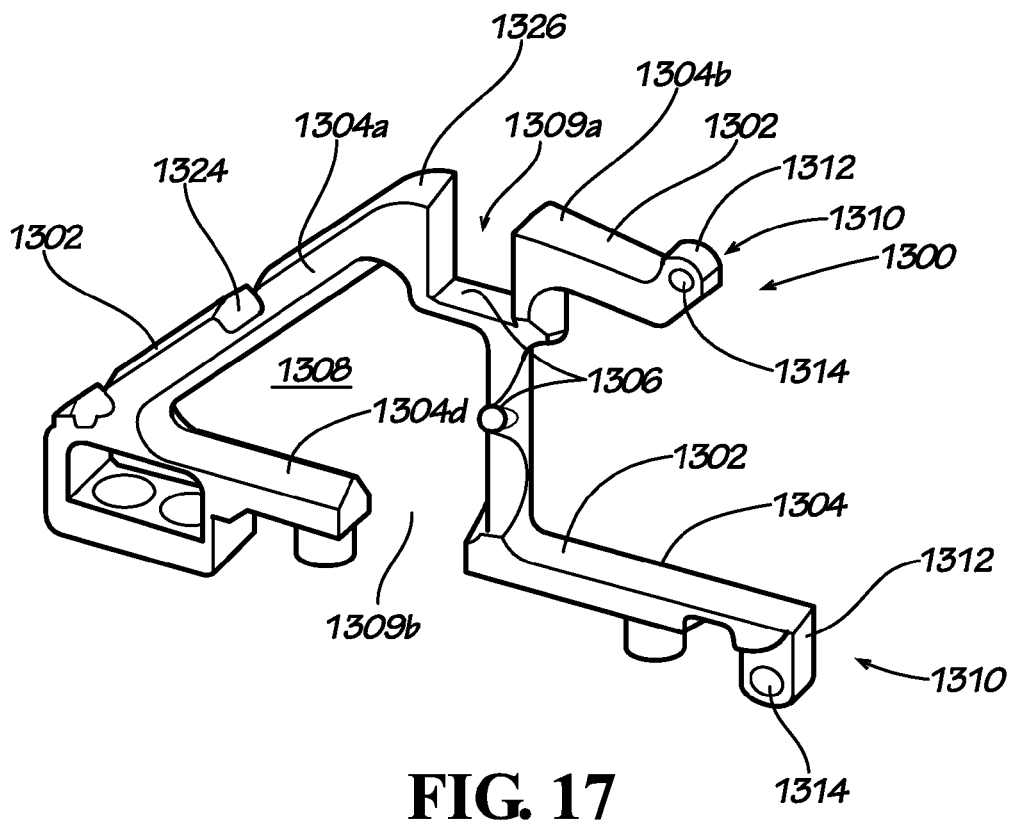
FIG. 17 shows yet another alternative embodiment of a first molded construct.

FIG. 17 shows another alternative embodiment of a first molded construct 1300. Like the constructs 200 and 1200, the construct 1300 defines one or more peripherally-positioned receptacle features 1324, 1326 configured to support a component (e.g., antenna 24). Like the construct 1200, the construct 1300 defines a skeletal frame 1302. Unlike the construct 1200, the construct 1300 defines a plurality of peripherally-extending wall segments 1304a, 1304b, 1304c, 1304d separated by respective peripheral gaps 1309a, 1309b. A plurality of struts 1306 span an interior region 1308 defined by the peripherally extending, wall segments and gaps.

The skeletal frame 1302 has a reduced overall surface area compared to the skeletal frame 1202, providing comparatively lower shear stresses and/or heat transfer during overmolding. Nonetheless, at least one of the wall segments 1304a, 1304 b, 1304c, 1304d is cantilevered from a portion of the frame 1302 (e.g., segment 1304b) and could deform to an undesirable degree during overmolding.

Figure 18:
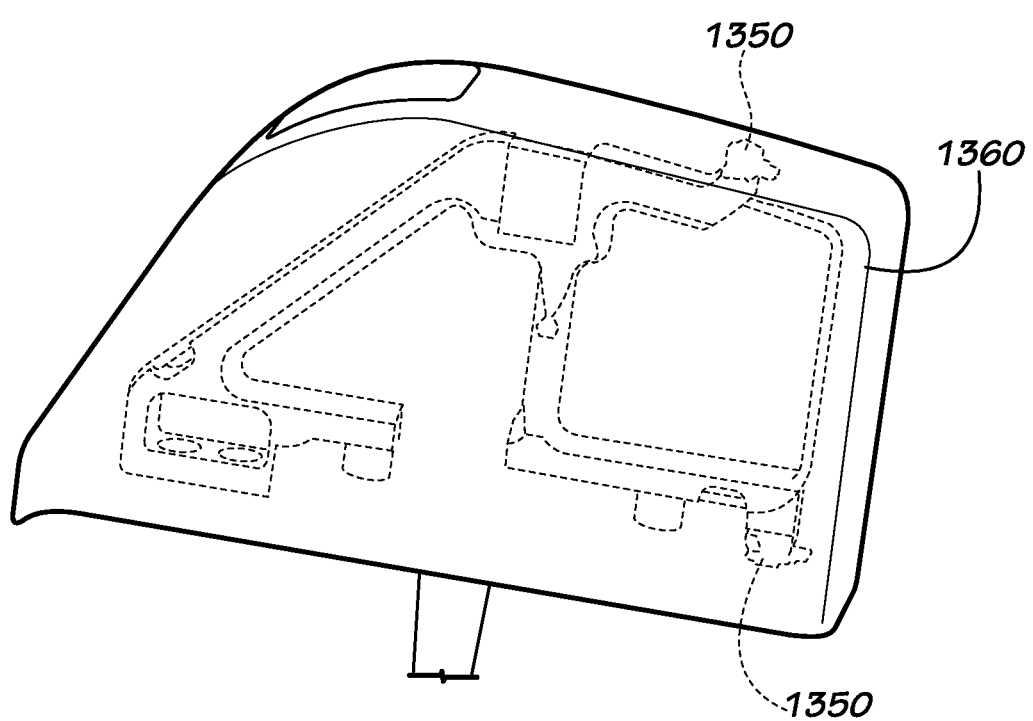
FIG. 18 shows the first molded construct shown in FIG. 17 within an over-molded second molded construct.

To reduce or eliminate such deformation of the cantilevered portion(s), segments 1304b and 1304c can define support features 1310 configured to engage a corresponding feature (e.g., a pin 1350 (FIG. 18)) of the overmolding mold 1360 (FIG. 18). For example, the features 1310 can include a boss 1312 defining an aperture 1314 extending through the boss, During placement of the first construct 1300 in the overmolding mold, a pin 1350 (FIG. 18) can extend through the aperture such that the boss 1312 engages an outer surface of the pin, supporting the cantilevered segment and reducing deformation of the peripheral wail portions.

While the foregoing discussion has been in terms of CRM devices, other implantable devices that would benefit from the inventive subject matter include implantable pain management devices, which are also based on a pulse generator and antenna.

Disclosed Principles are not Limited to Described Embodiments

This disclosure makes reference to the accompanying drawings which form a part hereof, wherein like numerals designate like parts throughout. The drawings illustrate specific embodiments, but other embodiments may be formed and structural changes may be made without departing from the intended scope of this disclosure. Directions and references (e.g., up, down, top, bottom, left, right, rearward, forward, etc.) may be used to facilitate discussion of the drawings but are not intended to be limiting. For example, certain terms may be used such as "up," "down,", "upper," "lower," "horizontal," "vertical," "left," "right," and the like. These terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" surface can become a "lower" surface simply by turning the object over. Nevertheless, it is still the same surface and the object remains the same. As used herein, "and/or" means "and" as well as "and" and "or."

Accordingly, this detailed description shall not be construed in a limiting sense, and following a review of this disclosure, those of ordinary skill in the art will appreciate the wide variety of interferometer systems that can be devised and constructed using the various concepts described herein. Moreover, those of ordinary skill in the art will appreciate that the exemplary embodiments disclosed herein can be adapted to various configurations without departing from the disclosed concepts. Thus, in view of the many possible embodiments to which the disclosed principles can be applied, it should be recognized that the above-described embodiments are only examples and should not be taken as limiting in scope. We therefore claim as our invention all that comes within the scope and spirit of the following claims.

All patent and non-patent literature cited herein is hereby incorporated by reference in its entirety for all purposes.

The invention claimed is:

1. A method of making an implantable medical device, the method comprising:
   providing at least a portion of a first mold cavity configured to form at least a first molded construct of an implantable medical device, the mold cavity having a receiving feature configured to hold or to receive a component during an overmolding process;
   introducing into the first mold cavity a moldable plastic material capable of taking the shape of the mold cavity, thereby forming a first molded construct of the device to a corresponding shape of the respective portion of the first mold cavity;
   positioning a component in the respective portion of the first mold cavity before the introduction of moldable plastic material, or on the first molded construct following introduction of the moldable plastic material, so that at least one segment of the component is securely disposed at a surface of the formed first molded construct;
   providing at least a portion of a second mold cavity configured to form at least a portion of an implantable medical device;
   placing the formed first molded construct with the positioned component into the respective portion of the second mold cavity; and
   introducing into the second mold cavity a moldable plastic material capable of taking the shape of the second mold cavity, thereby forming a second molded construct of the device to a corresponding shape of the second mold cavity, the first and second molded constructs being moldably fused together at an interface therebetween, wherein the component is disposed at the interface of the first molded construct and the second molded construct, wherein at least a portion of the component is disposed in an elongate path along the interface and wherein the second molded construct overlies the first construct and the portion of the component disposed along the elongate path so as to surround that portion of the component and to hermetically seal it.

2. A method according to claim 1, wherein the portion of the component comprises a first portion of the component disposed in a channel formed in the first molded construct and a second portion extending outwardly of the channel, wherein the second molded construct overlies the second portion of the component extending outwardly of the channel.

3. A method according to claim 1, wherein the component comprises at least one antenna or a conductor element that is exposed at a surface of the implantable medical device, free of material of the first construct and the second construct.

4. A method according to claim 1, wherein the component comprises a first antenna or a first conductor element disposed along the elongate path, the method further comprising providing a second antenna or a second conductor element that is exposed at a surface of the device, free of material of the first construct and second construct.

5. A method according to claim 1, wherein at least a region of the first molded construct is fusion-bonded to a corresponding region of the second molded construct.

6. A method according to claim 1 wherein the component is securely positioned adjacent a surface of the first molded construct after the forming of the first molded construct and before the formation of the second molded construct.

7. A method according to claim 1, wherein:
the first molded construct defines one or more peripherally-positioned receptacle features configured to support a corresponding component, wherein a surface area of the first molded construct is less than about 60% of a projected plan area of the first molded construct; and
the act of positioning the component in the respective portion of the mold cavity comprises positioning the component to extend longitudinally of one of the receptacle features.

8. A method according to claim 7, wherein the surface area of the first molded construct is less than about 30% of the projected plan area of the first molded construct.

9. A method according to claim 7, wherein the component comprises an elongate component and the first molded construct comprises a skeletal frame configured to retain the elongate component during the act of introducing into the second mold cavity a moldable plastic material capable of taking the shape of the second mold cavity.

10. A method according to claim 9, wherein the skeletal frame defines at least one cantilevered member configured to retain a corresponding portion of the elongate component.

11. A method according to claim 10, wherein the second mold cavity comprises a corresponding support element of a molding die, and wherein the act of placing the first molded construct into the respective portion of the second mold cavity comprises engaging the support element of the molding die with a portion of the cantilevered member.

12. The implantable medical device of claim 11, wherein the portion of the cantilevered member comprises a boss defining an aperture extending through the boss, wherein the act of engaging the support element of the molding die comprises extending a portion of the molding die through the boss and thereby supporting the cantilevered member of the skeletal frame.

13. A method according to claim 1, wherein at least a portion of the component is disposed in an elongate path along the interface.

14. A method according to claim 13, wherein the portion of the component comprises a first portion of the component disposed in a channel formed in the first molded construct and a second portion extending outwardly of the channel, wherein the second molded construct overlies the second portion of the component extending outwardly of the channel.

15. A method according to claim 13, wherein the second molded construct overlies the first construct and the portion of the component disposed along the elongate path so as to surround that portion of the component and to hermetically seal it.

16. A method according to claim 15, wherein the component comprises a first antenna or a first conductor element disposed along the elongate path, the method further comprising providing a second antenna or a second conductor element that is exposed at a surface of the device, free of material of the first construct and second construct.

17. A method of making an implantable medical device, the method comprising:
providing at least a portion of a first mold cavity configured to form at least a first molded construct of an implantable medical device, the mold cavity having a receiving feature configured to hold or to receive a component during an overmolding process;
introducing into the first mold cavity a moldable plastic material capable of taking the shape of the mold cavity, thereby forming a first molded construct of the device to a corresponding shape of the respective portion of the first mold cavity;
positioning a component in the respective portion of the first mold cavity before the introduction of moldable plastic material, or on the first molded construct following introduction of the moldable plastic material, so that at least one segment of the component is securely disposed at a surface of the formed first molded construct;
providing at least a portion of a second mold cavity configured to form at least a portion of an implantable medical device;
placing the formed first molded construct with the positioned component into the respective portion of the second mold cavity; and
introducing into the second mold cavity a moldable plastic material capable of taking the shape of the second mold cavity, thereby forming a second molded construct of the device to a corresponding shape of the second mold cavity, the first and second molded constructs being moldably fused together at an interface therebetween, wherein the component is disposed at the interface of the first molded construct and the second molded construct, wherein the component comprises at least one antenna or a conductor element that is exposed at a surface of the implantable medical device, free of material of the first construct and the second construct.

18. A method according to claim 17, wherein at least a portion of the component is disposed in an elongate path along the interface.

19. A method according to claim 18, wherein the portion of the component comprises a first portion of the component disposed in a channel formed in the first molded construct and a second portion extending outwardly of the channel, wherein the second molded construct overlies the second portion of the component extending outwardly of the channel.

20. A method according to claim 18, wherein the second molded construct overlies the first construct and the portion of the component disposed along the elongate path so as to surround that portion of the component and to hermetically seal it.

21. A method according to claim 20, wherein the component comprises a first antenna or a first conductor element disposed along the elongate path, the method further comprising providing a second antenna or a second conductor element that is exposed at a surface of the device, free of material of the first construct and second construct.

22. A method according to claim 17, wherein at least a region of the first molded construct is fusion-bonded to a corresponding region of the second molded construct.

23. A method according to claim 17 wherein the component is securely positioned adjacent a surface of the first molded construct after the forming of the first molded construct and before the formation of the second molded construct.

24. A method according to claim 17, wherein:
the first molded construct defines one or more peripherally-positioned receptacle features configured to support a corresponding component, wherein a surface area of the first molded construct is less than about 60% of a projected plan area of the first molded construct; and
the act of positioning the component in the respective portion of the mold cavity comprises positioning the component to extend longitudinally of one of the receptacle features.

25. A method according to claim 24, wherein the surface area of the first molded construct is less than about 30% of the projected plan area of the first molded construct.

26. A method according to claim 24, wherein the component comprises an elongate component and the first molded construct comprises a skeletal frame configured to retain the elongate component during the act of introducing into the second mold cavity a moldable plastic material capable of taking the shape of the second mold cavity.

27. A method according to claim 26, wherein the skeletal frame defines at least one cantilevered member configured to retain a corresponding portion of the elongate component.

28. A method according to claim 27, wherein the second mold cavity comprises a corresponding support element of a molding die, and wherein the act of placing the first molded construct into the respective portion of the second mold cavity comprises engaging the support element of the molding die with a portion of the cantilevered member.

29. The implantable medical device of claim 28, wherein the portion of the cantilevered member comprises a boss defining an aperture extending through the boss, wherein the act of engaging the support element of the molding die comprises extending a portion of the molding die through the boss and thereby supporting the cantilevered member of the skeletal frame.

30. A method of making an implantable medical device, the method comprising:
providing at least a portion of a first mold cavity configured to form at least a first molded construct of an implantable medical device, the mold cavity having a receiving feature configured to hold or to receive a component during an overmolding process;
introducing into the first mold cavity a moldable plastic material capable of taking the shape of the mold cavity, thereby forming a first molded construct of the device to a corresponding shape of the respective portion of the first mold cavity;
positioning a component in the respective portion of the first mold cavity before the introduction of moldable plastic material, or on the first molded construct following introduction of the moldable plastic material, so that at least one segment of the component is securely disposed at a surface of the formed first molded construct;
providing at least a portion of a second mold cavity configured to form at least a portion of an implantable medical device;
placing the formed first molded construct with the positioned component into the respective portion of the second mold cavity; and
introducing into the second mold cavity a moldable plastic material capable of taking the shape of the second mold cavity, thereby forming a second molded construct of the device to a corresponding shape of the second mold cavity, the first and second molded constructs being moldably fused together at an interface therebetween, wherein the component is disposed at the interface of the first molded construct and the second molded construct, wherein the first molded construct defines one or more peripherally-positioned receptacle features configured to support a corresponding component, a surface area of the first molded construct is less than about 60% of a projected plan area of the first molded construct, and the act of positioning the component in the respective portion of the mold cavity comprises positioning the component to extend longitudinally of one of the receptacle features.

31. A method according to claim 30, wherein the component comprises at least one antenna or a conductor element that is exposed at a surface of the implantable medical device, free of material of the first construct and the second construct.

32. A method according to claim 30, wherein at least a region of the first molded construct is fusion-bonded to a corresponding region of the second molded construct.

33. A method according to claim 30 wherein the component is securely positioned adjacent a surface of the first molded construct after the forming of the first molded construct and before the formation of the second molded construct.

34. A method according to claim 30, wherein the surface area of the first molded construct is less than about 30% of the projected plan area of the first molded construct.

35. A method according to claim 30, wherein the component comprises an elongate component and the first molded construct comprises a skeletal frame configured to retain the elongate component during the act of introducing into the second mold cavity a moldable plastic material capable of taking the shape of the second mold cavity.

36. A method according to claim 35, wherein the skeletal frame defines at least one cantilevered member configured to retain a corresponding portion of the elongate component.

37. A method according to claim 36, wherein the second mold cavity comprises a corresponding support element of a molding die, and wherein the act of placing the first molded construct into the respective portion of the second mold cavity comprises engaging the support element of the molding die with a portion of the cantilevered member.

38. The implantable medical device of claim 37, wherein the portion of the cantilevered member comprises a boss defining an aperture extending through the boss, wherein the act of engaging the support element of the molding die comprises extending a portion of the molding die through the boss and thereby supporting the cantilevered member of the skeletal frame.

* * * * *